United States Patent [19]

Foster et al.

[11] Patent Number: 4,581,352

[45] Date of Patent: Apr. 8, 1986

[54] THIENOTHIENYLGLYCYL CEPHALOSPORIN DERIVATIVES

[75] Inventors: Bennie J. Foster, Greenwood; David C. Hunden, Carmel; Edward R. Lavagnino, Indianapolis, all of Ind.

[73] Assignee: Eli Lilly and Company, Indianapolis, Ind.

[21] Appl. No.: 677,651

[22] Filed: Dec. 3, 1984

[51] Int. Cl.[4] .................. A61K 31/545; C07D 501/20; C07D 501/22; C07D 501/57
[52] U.S. Cl. ..................................... 514/202; 544/22; 544/28; 549/50; 548/183
[58] Field of Search ...................... 544/22, 28; 514/202

[56] References Cited

U.S. PATENT DOCUMENTS

| | | | |
|---|---|---|---|
| 3,733,322 | 5/1973 | Wright | 549/50 |
| 4,482,553 | 11/1984 | Cooper et al. | 424/246 |
| 4,490,370 | 12/1984 | Cooper | 544/16 |
| 4,492,693 | 1/1985 | Blascak et al. | 514/202 |
| 4,501,741 | 2/1985 | Graves | 544/22 |

FOREIGN PATENT DOCUMENTS

| | | | |
|---|---|---|---|
| 279039 | 2/1970 | Austria | 544/28 |
| 767108 | 7/1978 | U.S.S.R. | 549/50 |

OTHER PUBLICATIONS

Ott et al., 1984, Abstracts of the 24th Interscience Conference on Antimicrobial Agents and Chemotherapy, Abstract No. 227, "Chemistry and *In Vitro* Microbiology of Some New Orally Active Cephalosporins".

*Primary Examiner*—Donald G. Daus
*Assistant Examiner*—Robert Benson
*Attorney, Agent, or Firm*—Charles W. Ashbrook; Arthur R. Whale

[57] ABSTRACT

7-(Thienothienyl)glycylamido cephalosporins have good gram positive activity and favorable pharmacokinetics and are orally effective.

44 Claims, No Drawings

THIENOTHIENYLGLYCYL CEPHALOSPORIN DERIVATIVES

BACKGROUND OF THE INVENTION

The cephalosporin class of antibiotics has been extensively studied, and several members of the class are now routinely used to combat bacterial diseases caused by a broad spectrum of gram positive and gram negative microorganisms. The majority of such compounds are not effective orally, but rather are administered intramuscularly or intravenously, thus necessitating assistance from medically trained personnel. Moreover, since the compounds are effective against a broad spectrum of microorganisms, they generally are not employed for their specificity.

There remains a need for cephalosporin antibiotics that are orally effective and have a degree of specificity toward one or more groups of microorganisms. An object of this invention is to provide a group of compounds that satisfies these needs.

SUMMARY OF THE INVENTION

This invention concerns cephalosporin antibiotics. The invention is more particularly directed to a group of (thienothienyl)glycylamido cephalosporin derivatives having the formula

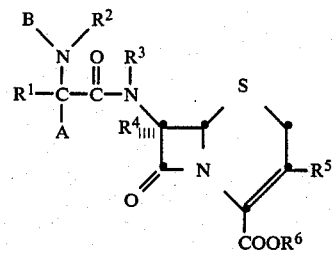

wherein: $R_1$ is

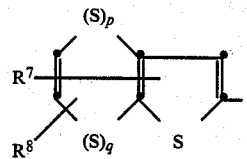

in which $R^7$ and $R^8$ independently are hydrogen, halo, hydroxy, $C_1$–$C_4$ alkyl, $C_1$–$C_4$ alkoxy, nitro, amino, $C_1$–$C_4$ alkanoylamino, $C_1$–$C_4$ alkylsulfonylamino, and when $R^7$ and $R^8$ are on adjacent carbon atoms, they can be taken together to form methylenedioxy;

p and q independently are 0 or 1, provided p plus q equal 1;

A and B both are hydrogen, or taken together complete a double bond;

$R^2$ is hydrogen, an amino protecting group, hydroxy, or methoxy, and $R^3$ is hydrogen, or $R^2$ and $R^3$ taken together are

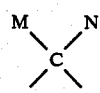

where M and N independently are $C_1$–$C_4$ alkyl;

$R^4$ is hydrogen, methoxy or methylthio;

$R^5$ is hydrogen, methoxy, methyl, halo, methoxymethyl, or vinyl;

$R^6$ is hydrogen, a salt forming cation group, or a carboxy protecting group; and the pharmaceutically acceptable acid addition salts thereof; with the proviso that $R^2$ is hydroxy or methoxy only when A and B complete a double bond, and that A and B both are hydrogen when $R^3$ is other than hydrogen.

Preferred compounds provided by the invention include those of the above formula wherein $R^1$ is

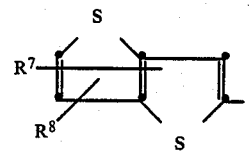

and $R^7$ and $R^8$ are as defined above. Within this group, preferred compounds include those wherein $R^2$ is hydrogen, an amino protecting group, hydroxy or methoxy, and $R^6$ is hydrogen or a carboxy protecting group.

Another preferred group of compounds are those wherein $R^1$ is

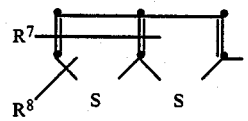

and $R^7$ and $R^8$ are as defined above. Especially preferred compounds within this group include those wherein A, B, $R^2$, $R^3$, $R^4$ and $R^6$ all are hydrogen.

A particularly preferred group of compounds provided by this invention are defined by the formula

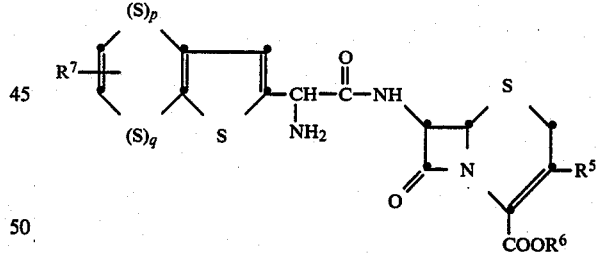

wherein p, q, $R^5$, $R^6$ and $R^7$ are as defined above. The most preferred compounds are those within this group wherein $R^7$ is hydrogen, halo, hydroxy or methoxy, $R^5$ is methyl or chloro, and $R^6$ is hydrogen or a salt forming group such as sodium or potassium cation.

An additional embodiment of this invention is a pharmaceutical formulation comprising a thienothienylglycylamido cephalosporin derivative as defined above admixed with a pharmaceutical carrier, diluent or excipient therefor. A preferred formulation is one suitable for oral administration.

Yet another embodiment of this invention is a method for treating bacterial infections in animals comprising administering an effective amount of an antibacterial compound of the above formula. In a preferred method of treatment, the thienothienylglycyl cephalosporin derivative is administered orally to treat diseases caused by gram positive microorganisms.

DETAILED DESCRIPTION OF THE INVENTION

In the above formulas defining the compounds provided by this invention, $R^1$ defines a thieno[3,2-b]-thien-2-yl group of the formula

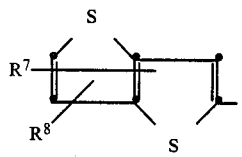

or a thieno[2,3-b]thien-2-yl group of the formula

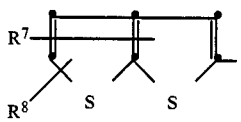

These thienothienyl groups can be unsubstituted, for instance when $R^7$ and $R^8$ both are hydrogen; or monosubstituted, for instance when one of $R^7$ or $R^8$ is hydrogen and one is other than hydrogen; or di-substituted, for instance when $R^7$ and $R^8$ both are other than hydrogen. $R^7$ can be located at the 3-position of the bicyclic ring system, or at one of the other two positions available for substitution.

$R^7$ and $R^8$ are defined above to include $C_1$–$C_4$ alkyl, $C_1$–$C_4$ alkoxy, halo, $C_1$–$C_4$ alkanoylamino and $C_1$–$C_4$ alkylsulfonylamino. The term "$C_1$–$C_4$ alkyl" carries its art-recognized meaning of straight and branched lower alkyl carbon chains such as methyl, ethyl, isopropyl, n-propyl, iso-butyl and tert.-butyl. Similarly, "$C_1$–$C_4$ alkoxy" refers to lower alkyl groups bonded to the thienothienyl bicyclic ring through an oxygen atom. Typical $C_1$–$C_4$ alkoxy groups include methoxy, ethoxy, n-propoxy, n-butoxy and iso-butoxy. The term "halo" as used herein includes fluoro, chloro, bromo and iodo. Preferred halo groups include chloro and fluoro.

$R^7$ and $R^8$ also represent $C_1$–$C_4$ alkanoylamino and $C_1$–$C_4$ alkylsulfonylamino. Typical alkanoylamino groups include formylamino,, acetylamino, and isobutyrylamino. Typical $C_1$–$C_4$ alkylsulfonylamino groups are methylsulfonylamino, ethylsulfonylamino and n-butylsulfonylamino.

When $R^7$ and $R^8$ are on adjacent carbon atoms, they can be taken together to form a methylenedioxy group, for example to form an $R^1$ substituent such as

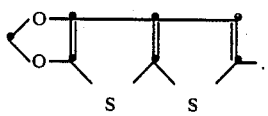

$R^2$ in the above formula defines a substituent on the glycyl nitrogen atom, and includes hydrogen and an amino protecting group. The term "amino protecting group" refers to any of the art-recognized substituents that can be attached to an amino nitrogen atom and which is readily removed when desired. Such protecting groups are often employed during preparation of the compounds of the invention, and serve to improve solubility in organic solvents and to decrease the likelihood of unwanted side reactions occurring as a result of the presence of a free amino group. While the compounds wherein $R^2$ is a protecting group are expected to have biological activity, it is contemplated that the most biologically desirable compounds will be those wherein $R^2$ is hydrogen. The compounds wherein $R^2$ is an amino protecting group are thus primarily useful as intermediates in the synthesis of the more preferred free amino compounds.

The precise nature of the amino protecting group is not critical to the invention, and any of the well known protecting groups can be employed. Typical amino protecting groups are described by J. W. Barton in "Protective Groups in Organic Chemistry," J. F. McOmie, Ed., Plenum Press, New York, N.Y., 1973, Chapter 2, and by Greene in "Protective Groups in Organic Synthesis," John Wiley and Sons, New York, N.Y., 1981, Chapter 7. Both of these references are incorporated herein by reference for their teaching of amino protecting groups.

The most common amino protecting groups to be employed include $C_1$–$C_{10}$ alkanoyl groups such as formyl, acetyl, dichloroacetyl, propionyl, hexanoyl 3,3-diethylhexanoyl, γ-chlorobutyryl, and the like; $C_1$–$C_{10}$ alkoxycarbonyl and $C_6$–$C_{15}$ aryloxycarbonyl groups such as tert.-butoxycarbonyl, benzyloxycarbonyl, allyloxycarbonyl, 4-nitrobenzyloxycarbonyl and cinnamoyloxycarbonyl; halo-$C_1$–$C_{10}$ alkoxycarbonyl such as 2,2,2-trichloroethoxycarbonyl; and $C_6$–$C_{20}$ arylalkyl and lower alkenyl groups such as benzyl, phenethyl, allyl, trityl, and the like. Other commonly used amino protecting groups are those in the form of enamines prepared with β-keto-esters such as methyl or ethyl acetoacetate.

$R^2$ in the above formula, in addition to representing hydrogen or an amino protecting group, also, when taken together with $R^3$, completes a ring system to provide compounds of the formula

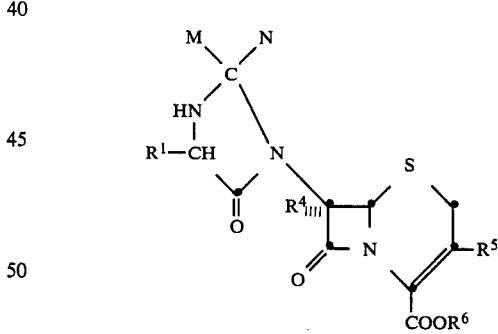

where $R^1$, $R^4$, $R^5$, $R^6$, M and N are as defined above. Typical of these compounds are the acetonides, for example those wherein M and N both are methyl. Such compounds are particularly useful as long-acting antibacterial agents and pro-drugs.

$R^6$ in the above formula is hydrogen; a salt forming group such as ammonium or an alkali metal cation, for example lithium, sodium or potassium; or a carboxy protecting group. The term "carboxy protecting group" refers to the art-recognized groups commonly employed to block or protect the carboxylic acid functionality of a cephalosporin molecule during chemical reactions involving other functional sites in the molecule, and which can be readily removed when desired by common hydrolytic or hydrogenolytic techniques.

Typical carboxy protecting groups to be employed according to this invention include those described by E. Haslam in "Protective Groups in Organic Chemistry,", supra, Chapter 5, and by Green in "Protective Groups in Organic Synthesis," supra, Chapter 5, which are incorporated herein by reference. Examples of the commonly employed carboxy protecting groups include $C_1$–$C_{10}$ alkyl groups such as methyl, tert.-butyl, decyl; halo-$C_1$–$C_{10}$ alkyl such as 2,2,2-trichloroethyl, and 2-iodoethyl; $C_6$–$C_{20}$ arylalkyl such as benzyl, 4-methoxybenzyl, 4-nitrobenzyl, triphenylmethyl, diphenylmethyl; $C_1$–$C_{10}$ alkanoyloxymethyl such as acetoxymethyl, propionoxymethyl and the like; and groups such as phenacyl, 4-halophenacyl, allyl, dimethylallyl, tri($C_1$–$C_3$ alkyl)silyl such as trimethylsilyl, β-p-toluenesulfonylethyl, β-p-nitrophenylthioethyl, 2,4,6-trimethylbenzyl, β-methylthioethyl, phthalimidomethyl, 2,4-dinitrophenylsulphenyl, 2-nitrobenzhydryl and related groups. Protecting groups such as acyloxymethyl and the like are also useful as biologically cleavable esters and can be employed for slow release therapeutic agents when attached to the cephalosporin.

The thienothienylglycyl cephalosporin derivatives provided by this invention can be prepared by any of several methods. A preferred method comprises reacting a 7-aminocephalosporin nucleus with a thienothienylglycine derivative according to the following scheme:

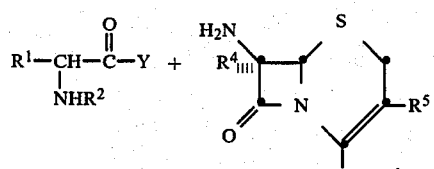

wherein $R^1$, $R^2$, $R^4$, $R^5$ and $R^6$ are as defined above, and Y is a leaving group such as hydroxy; halo, for instance chloro, bromo, or iodo; lower alkanoyloxy such as formyloxy, acetoxy or the like. Typical thienothienylglycine derivatives commonly employed in such direct coupling reactions include those of the formula

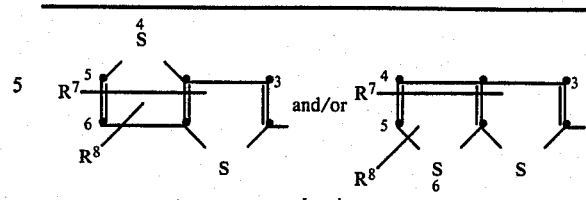

wherein:

| $R^7$ | $R^8$ | $R^2$ | Y |
|---|---|---|---|
| H | H | chloroacetyl | OH |
| H | H | formyl | Cl |
| H | H | H | Cl (as a hydrochloride) |
| H | H | chloroacetyl | OH |
| H | H | formyl | Cl |
| H | H | H | Cl (as a hydrochloride) |
| H | H | formyl | OCHO |
| 5-Cl | H | trichloroacetyl | OH |
| H | H | tert.-butoxycarbonyl | OH |
| 5-OCH$_3$ | H | 4-chlorobutyryl | OH |
| 3-OCH$_3$ | 4-Cl | tert.-butoxycarbonyl | Cl |
| 3-OCH$_3$ | 5-Br | benzyl | Br |
| 4-OCH$_2$CH$_3$ | H | trimethylsilyl | OCHO |
| 4-OCH$_3$ | 5-OCH$_3$ | p-nitrobenzyl | OCOCH$_3$ |
| 3-Cl | 4-NO$_2$ | acetyl | OH |
| 4-Br | 5-NH$_2$ | benzyloxycarbonyl | Br |
| 4-F | H | tert.-butoxycarbonyl | Cl |
| 5-CH$_3$ | H | allyloxycarbonyl | OH |
| 4-I | 5-acetylamino | 2,2,2-trichloroethoxycarbonyl | Cl |
| 4-CH$_3$ | H | H | Br (hydrobromide) |
| 3-CH$_3$ | 5-CH$_2$CH$_3$ | formyl | Cl |
| 4-CH$_2$CH$_3$ | H | acetyl | OH |
| 4-CH$_2$CH$_2$CH$_3$ | 5-F | benzoyl | HCHO |
| H | 5-methylsulfonylamino | H | Cl (hydrochloride) |
| H | 5-Cl | allyloxycarbonyl | OCOCH$_3$ |
| H | H | —C=CHCOOCH$_3$<br>\|<br>CH$_3$ | Cl |

The thienothienylglycine derivatives thus described are new compounds and are provided as a further embodiment of this invention. The compounds are generally prepared by cyclizing an appropriately substituted thioalkenyl thiophene to provide a thienothien-2-yl carboxylic acid, an converting the acid to a glycyl moiety. The synthesis is illustrated by the following reaction scheme:

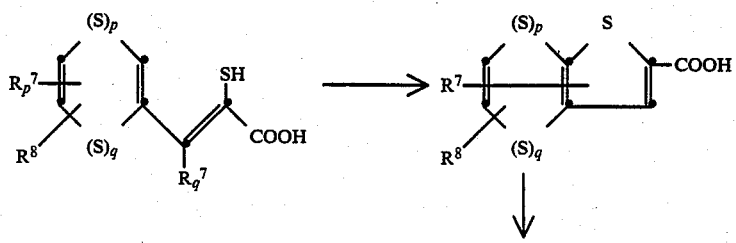

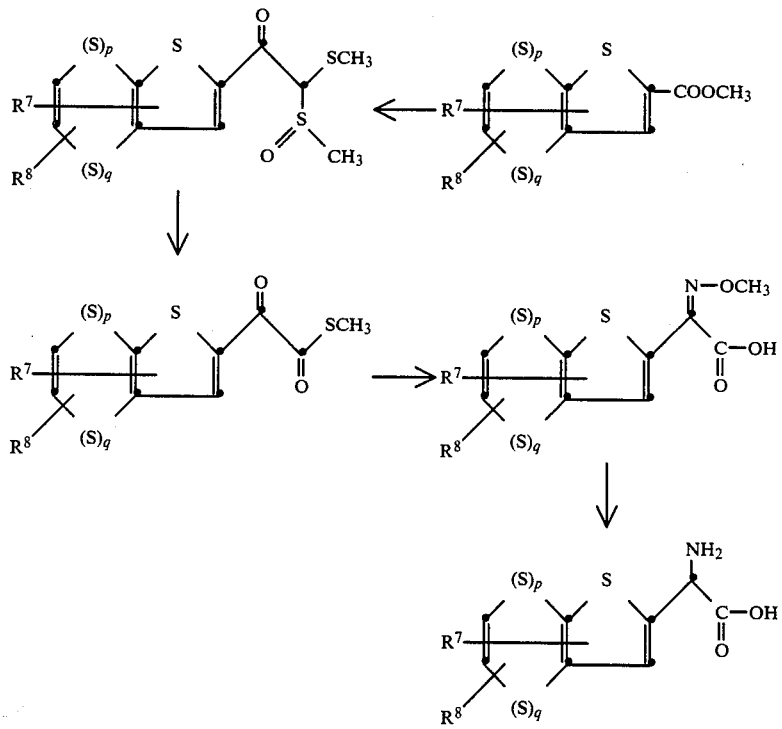

The thioalkenyl thiophene can be cyclized by first converting it to a chlorothio derivative by reaction with chlorine. The chlorothio derivative is readily cyclized by heating at about 100° to about 150° C. The carboxy substituted thienothiophene that is produced can be esterified by normal methods, for instance by reaction with diazomethane or the like. The thienothien-2-yl carboxylate is next reacted with a sulfide derivative such as methyl methylthiomethyl sulfoxide (MMTS) to produce a thienothiophene that is readily converted to a glyoxyl thio derivative. Reaction of the thienothienyl glyoxyl derivative with an alkoxyamine such as methoxyamine provides an oxime derivative of the thienothienyl glycine. The cephalosporin nucleus can be acylated with the glycine oxime or the oxime can be converted to the glycine prior to acylation.

The cephalosporin nuclei required for the synthesis of the present compounds are readily available or can be prepared by methods well known in the art. For example, the 3-halo cephalosporin nuclei can be prepared by the methods taught in U.S. Pat. No. 3,925,372. 3-Methyl cephalosporins are available by ring expansion of penicillin sulfoxides and subsequent side chain cleavage. The 3-vinyl cephem nucleus is available by the method of U.S. Pat. No. 3,994,884.

Typical cephalosporin nuclei that will be employed in the synthesis of compounds of the present invention are illustrated below:

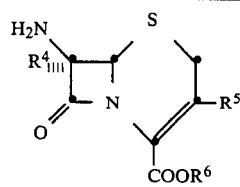

| $R^4$ | $R^5$ | $R^6$ |
|---|---|---|
| H | $CH_3$ | H |
| H | $CH_3$ | tert.-butyl |
| H | Cl | p-nitrobenzyl |
| $CH_3O$ | H | methyl |
| $CH_3S$ | $CH_3$ | H |
| H | $-CH_2OCH_3$ | 2,2,2-trichloroethyl |
| H | $-CH=CH_2$ | benzyl |
| H | $OCH_3$ | allyl |
| $CH_3O$ | Br | trimethylsilyl |
| $CH_3S$ | H | tert.-butyl |
| H | I | Na |

The coupling of a thienothienylglycine derivative with a 7-aminocephalosporin nucleus can be accomplished employing common techniques of acylation. For example, a thienothienylglycyl acylating agent, wherein Y in the above formula is a leaving group such as halo, especially chloro or bromo, or alkanoyloxy such as formyloxy or acetoxy, can be reacted with a cephalosporin nucleus employing standard acylation conditions. During such acylation reaction, it generally is preferred that $R^2$ in the above formula be an amino protecting group and that $R^6$ be a carboxy protecting group. These protecting groups serve to minimize unwanted side reactions and to increase solubility characteristics of the respective reactants.

The acylation reaction generally is accomplished by combining approximately equimolar quantities of a thienothienylglycyl acylating agent (i.e. an acid halide or mixed acid anhydride) with the 7-aminocephalosporin nucleus. The acylation reaction normally is carried out in a mutual solvent such as benzene, chloroform, dichloromethane, toluene, N,N-dimethylformamide, acetonitrile, or the like, and routinely is substantially complete after about 1 to about 12 hours when conducted at a temperature of about −20° to about 60° C. About an equimolar quantity of a base such as pyridine, triethylamine, N,N-dimethyl aniline, sodium carbonate or the like, can be employed in the reaction if desired to act as an acid scavenger. The product may be isolated from the reaction mixture by simply removing the reaction solvent, for instance by evaporation under reduced pressure, and further purification can be accomplished if needed employing routine techniques such as chromatography, crystallization, solvent extraction, and related methods.

An alternative and preferred method for coupling a thienothienylglycine derivative to a 7-aminocephalosporin nucleus to produce compounds of the invention employs a coupling reagent such as those routinely used in the synthesis of peptides. Typical coupling reagents that can be employed include carbodiimides such as N,N′-diethylcarbodiimide, N,N-diisopropylcarbodiimide, and N,N-dicyclohexylcarbodiimide (DCC); carbonyl coupling reagents such as carbonyldiimidazole; isoxazolinium salts such as N-ethyl-5′-phenylisoxazolinium-3′-sulfonate; and quinoline compounds such as N-ethoxycarbonyl-2-ethoxy-1,2-dihydroquinoline (EEDQ).

The coupling of a 7-aminocephalosporin nucleus with a thienothienylglycine derivative employing a peptide coupling reagent generally is accomplished by combining approximately equimolar quantities of a 7-aminoceph-3-em-4-carboxylic acid, a thienothienylglycine, and a peptide coupling reagent according to the following scheme;

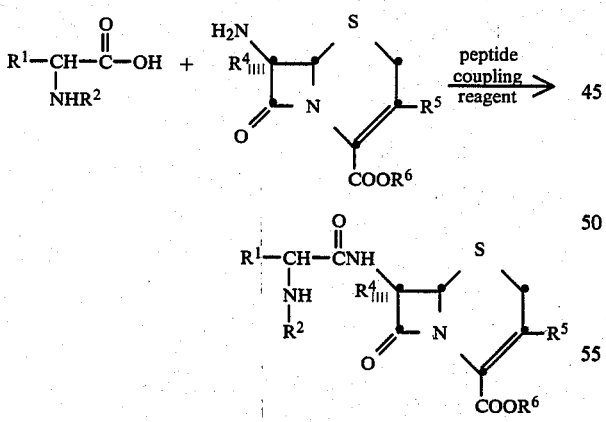

wherein $R^1$, $R^2$, $R^4$, $R^5$ and $R^6$ are as defined above. Preferably $R^2$ is an amino protecting group and $R^6$ is hydrogen or a carboxy protecting group during such coupling reactions. Any such protecting groups can be subsequently removed by standard methods to give the active antibiotic of the invention.

The coupling reaction normally is conducted in a mutual solvent such as dichloromethane, acetone, water, acetonitrile, N,N-dimethylformamide, chloroform, or the like, and routinely is substantially complete when carried out for about ten to about ninety minutes at a temperature of about −20° to about 60° C. Longer reaction periods are not detrimental to the product and can be employed if desired. The product, a thienothienylglycyl cephalosporin derivative of the invention, is readily isolated by simply removing the reaction solvent, for instance by evaporation under reduced pressure. The product can be purified if needed by standard methods such as acid-base extraction, chromatography, salt formation or the like.

Yet another alternative method for preparing compounds of the invention comprises chemically modifying a position other than the side chain of a thienothienylglycyl cephalosporin. For example, a 3-exomethylene cephalosporin nucleus can be acylated with a thienothienylglycyl derivative to form a thienothienylglycyl 3-exomethylene cephalosporin. The latter compound can be converted by known methods to compounds of the invention. For instance, ozonolysis of a thienothienylglycyl 3-exomethylene cephalosporin affords a 3-hydroxy compound. Halogenation of a 3-hydroxy compound affords the 3-halo thienothienylglycyl cephalosporins of the invention, while reaction with a base and a methylating agent affords the 3-methoxy compounds of the invention.

Still another method for preparing compounds of the invention employs a thienothienyl oxime derivative of the formula

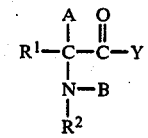

wherein $R^1$ and Y have the above-defined meanings, A and B are taken together to form a bond, and $R^2$ is hydroxy or methoxy. When $R^2$ is hydroxy, it generally is protected with trimethylsilyl, p-nitrobenzyl, or similar hydroxy protecting group during the coupling reaction. Such thienothienyl oxime derivatives can be coupled to a cephalosporin nucleus by any of the methods described above to provide a compound of the formula

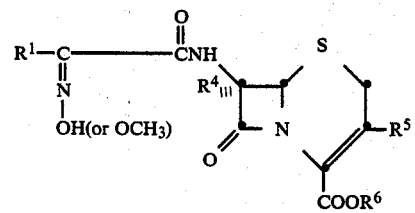

wherein $R^1$, $R^4$, $R^5$, and $R^6$ are as defined above. These compounds are useful as intermediates since they are readily reduced by normal methods to give the preferred thienothienylglycyl compounds of the invention. Additionally, the oximes of the above formula wherein $R^6$ is hydrogen or a salt forming group are useful antibiotics.

Compounds of the invention that bear a nitro group or the thienothienylglycyl side chain can be modified to provide other compounds of the invention. For example, the nitro substituent can be reduced by routine reduction or hydrogenation procedures to give the corresponding amino substituted thienothienylglycyl cephalosporin derivative, which if desired can be acylated by reaction with a $C_1$–$C_4$ alkanoyl halide or anhydride or a $C_1$–$C_4$ alkylsulfonyl halide to provide the corresponding alkanoylamino or alkylsulfonylamino thienothienylglycylamido cephalosporin of the invention.

Similarly, compounds of the invention wherein $R^2$ and $R^3$ are taken together to form the group

are prepared by reacting a ketone of the formula

with a compound of the invention wherein $R^2$ and $R^3$ both are hydrogen, generally in the presence of a catalytic amount of an acid such as methanesulfonic acid or the like. The cyclic compounds thus produced, for instance the preferred acetonides wherein M and N both are methyl, are particularly useful as oral antibiotics since they are effective over prolonged periods of time.

Other compounds of the invention that are expected to be particularly long acting antibiotics are those wherein $R^2$ is an alkanoyl amino protecting group such as formyl or acetyl. Such compounds are conveniently prepared by simply reacting a thienothienylglycylamido cephalosporin, wherein $R^2$ is hydrogen, with a $C_1$–$C_{10}$ alkanoyl acylating agent, for instance formyl chloride or acetic anhydride. These N-acylated products are expected to act not only as antibiotics in themselves, but also as pro-drugs in that they will be hydrolyzed in an animal system to the parent thienothienylglycyl derivative.

It should be noted that since the thienothienylglycyl side chains of the cephalosporins of this invention contain one asymmetric carbon atoms, for example when A is hydrogen, the compounds of the invention can exist in the form of optical isomers, namely the D and the L isomers of the side chain. The compounds of the invention can be employed as a DL-mixture to treat bacterial infections in animals, or if desired the isomers can be separated and employed individually. While both isomers are effective antibacterial agents, one isomer appears to be more potent than the other and is designated herein as the D isomer, and accordingly is a preferred embodiment of the invention.

Separation or resolution of the isomers can be accomplished by routine methods carried out on the cephalosporin product of the invention or on the thienothienylglycine side chain that is employed as a starting material. Separation of isomers generally will be accomplished by high performance chromatography, enzymatic resolution, crystallization, or chemical resolution. A particularly preferred method for obtaining D-(thienothien-2-yl)glycine comprises reacting the D,L-mixture with benzaldehyde and optically active tartaric acid according to the method of U.S. Pat. No. 3,976,680. Another preferred method of resolution employs an N-acyl L-amino acid amidohydrolase enzyme, for instance according to the method described in U.S. Pat. No. 3,386,888.

As noted above, preferred compounds of the invention are those wherein $R^2$ in the above formula is hydrogen. Such compounds, being primary amines, are basic in nature and readily form pharmaceutically acceptable salts by reaction with acids. Typical acids commonly employed to form salts include inorganic acids such as hydrogen chloride, hydrogen bromide, sulfuric acid, phosphoric acid; as well as organic acids such as acetic acid, trifluoroacetic acid, succinic acid, methanesulfonic acid, oxalic acid, para-toluenesulfonic acid, and the like. The compounds of the invention wherein both $R^2$ and $R^6$ are hydrogen readily form an internal acid addition salt, namely a zwitterion.

Examples of typical classes of thienothienylglycyl cephalosporins, as well as specific compounds provided by this invention, include those listed below:

Preferred Compounds of the formula

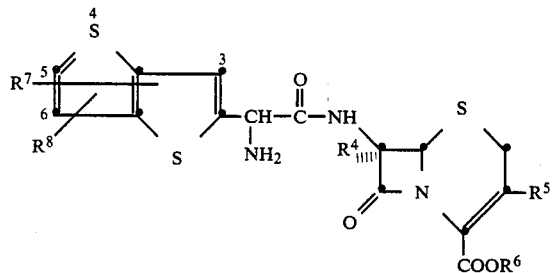

and/or

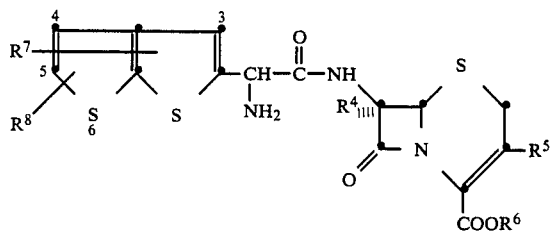

-continued

| R⁷ | R⁸ | R⁴ | R⁵ | R⁶ |
|---|---|---|---|---|
| H | H | H | $CH_3$ | H |
| H | H | H | Cl | H |
| H | H | H | $CH=CH_2$ | H |
| H | 4-Cl | H | H | $Na^+$ |
| 3-OH | H | $CH_3O-$ | $CH_2OCH_3$ | H |
| 4-Br | 5-$CH_3$ | H | $OCH_3$ | H |
| 4-$CH_3$ | 5-$OCH_2CH_3$ | $CH_3S-$ | Br | $NH_4^+$ |
| 5-F | H | H | $CH_3$ | H |
| H | 5-$NO_2$ | H | $CH_3$ | $K^+$ |
| H | 5-$NH_2$ | H | $CH_3$ | H |
| H | 5-$NHCOCH_3$ | $CH_3O-$ | F | H |
| 3-Cl | 5-$NHSO_2CH_2CH_3$ | H | $CH=CH_2$ | H |
| 5-$OCH_2CH(CH_3)_2$ | H | H | H | tert-butyl |
| 4-OH | 5-$CH_3$ | $CH_3S-$ | $CH_2OCH_3$ | p-nitrobenzyl |
| H | H | H | $CH_3$ | $CH_2CH=CH_2$ |
| H | H | H | Cl | $CH_2CCl_3$ (hydrochloride) |
| 5-Cl | H | H | $OCH_3$ | trimethylsilyl |
| 5-$CH_3$ | H | H | $CH_3$ | H |
| 4-$CH_3$ | H | H | $CH_3$ | H |

Compounds of the formula

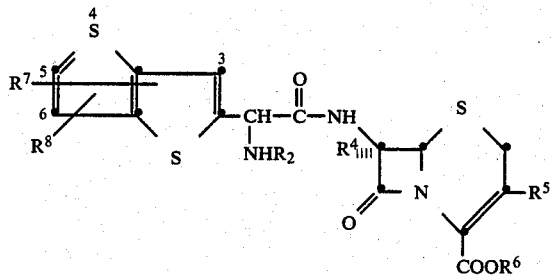

and/or

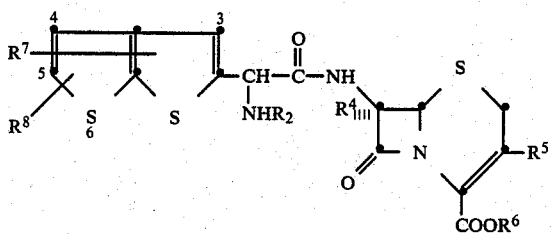

| R⁷ | R⁸ | R² | R⁴ | R⁵ | R⁶ |
|---|---|---|---|---|---|
| H | H | COOtert.-butyl | H | $CH_3$ | H |
| H | H | $COOCH_2CH=CH_2$ | H | Cl | H |
| H | 5-$OCH_3$ | $COCH_3$ | $CH_3O$ | H | H |
| 3-Cl | 5-$OCH_3$ | $COOCH_2CCl_3$ | H | $OCH_3$ | $CH_2CCl_3$ |
| 4-$CH_3$ | H | $CH_2\phi$ | H | $CH_2OCH_3$ | p-nitrobenzyl |
| 5-Br | 6-Br | $C(\phi)_3$ | $CH_3S$ | Br | $CH_3$ |
| H | 5-OH | CHO | H | $CH=CH_2$ | $CH_2OCOCH_3$ |
| 5,6-methylenedioxy | | $Si(CH_3)_3$ | H | I | $Si(CH_3)_3$ |
| 5-$CH_2CH_2CH_3$ | H | | H | $CH_3$ | |

Compounds of the formula

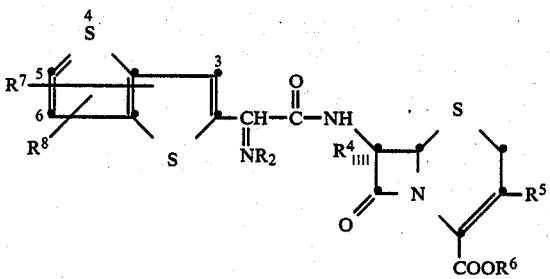

or

-continued

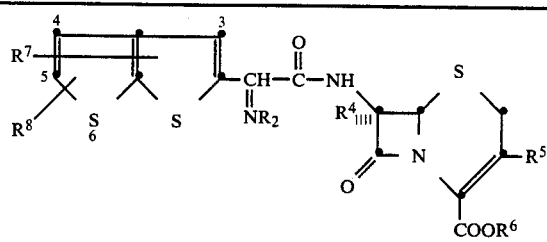

| R⁷ | R⁸ | R² | R⁴ | R⁵ | R⁶ |
|---|---|---|---|---|---|
| H | H | OH | H | $CH_3$ | H |
| H | H | $OCH_3$ | H | Cl | H |
| H | H | OH | $CH_3O$ | $CH_2OCH_3$ | H |
| H | H | $OCH_3$ | H | H | tert.-butyl |
| H | 5-F | $OCH_3$ | H | $CH=CH_2$ | p-nitrobenzyl |
| 3-Cl | 5-$OCH_3$ | OH | $CH_3S$ | F | $CH_2CCl_3$ |
| 3-Br | H | $OCH_3$ | H | $CH_3$ | $Na^+$ |
| 5-Cl | 6-Cl | $OCH_3$ | H | $CH_3$ | $CH_3$ |
| 5-$NH_2$ | H | OH | H | Cl | $CH_2CH=CH_2$ |
| 5-$NHCOCH_3$ | H | $OCH_3$ | H | $OCH_3$ | $CH(Cl)_2$ |
| 5,6-methylene-dioxy | | $OCH_3$ | H | $CH_3$ | H |

Compounds of the formula

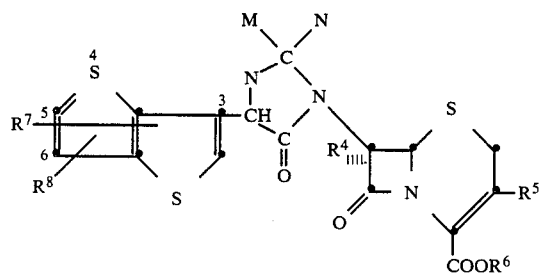

and/or

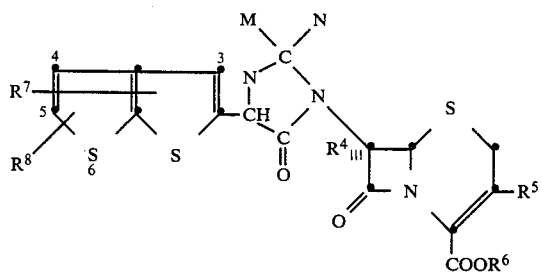

| R⁷ | R⁸ | M | N | R⁴ | R⁵ | R⁶ |
|---|---|---|---|---|---|---|
| H | H | $CH_3$ | $CH_3$ | H | $CH_3$ | H |
| H | 5-F | $CH_3$ | $CH_3$ | H | Cl | $Na^+$ |
| H | 6-$OCH_3$ | $CH_3$ | $CH_3$ | $CH_3O$ | $OCH_3$ | tert.-butyl |
| 3-Cl | H | $CH_3$ | $CH_3$ | $CH_3S$ | H | H |
| 3-$OCH_3$ | 5-$CH_3$ | $CH_2CH_3$ | $CH_3$ | H | $CH_3$ | $CH(O)_2$ |
| 5-F | 6-F | $CH_3$ | $CH_3$ | H | $CH=CH_2$ | $CH_2CH=CH_2$ |

The synthesis of the compounds provided by this invention is further illustrated by the following preparations and working examples. The examples are illustrative only and are not intended to limit the invention in any respect.

PREPARATION 1

α-Methoxyimino-α-(thieno[3,2-b]thien-2-yl)-acetic acid

A. Preparation of thieno[3,2-b]thien-2-yl carboxylic acid.

To a stirred solution of 100 g (0.89 mole) of thiophene-2-carboxaldehyde and 119 g (0.89 mole) of 2-thioxo-4-thiazolidinone (Rhodanine) in 600 ml of hot (100° C.) glacial acetic acid were added portion-wise 260 g of sodium acetate. The reaction mixture was heated at reflux for thirty minutes and then poured into 3 liters of water. The precipitated solid was collected by filtration, washed with diethyl ether and dried to provide 187 g of a compound of the formula

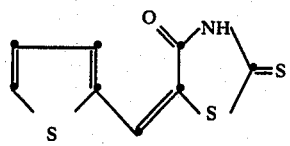

m.p. 228° C.

Analysis calculated for $C_8H_5NOS_3$ Theory: C, 42.27; H, 2.22; N, 6.16; Found: C, 42.15; H, 2.32; N, 6.41.

B. Preparation of

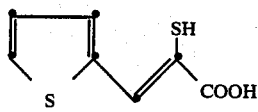

The product from Preparation A (113 g) was added to a stirred solution of 1 kg of 8% aqueous sodium hydroxide (w/v) and the mixture was heated at 45° C. for thirty minutes. The mixture was cooled to 5° C. and diluted by addition of 1 liter of 3N hydrochloric acid. The precipitated solid was collected by filtration, washed with water and dried to afford 93.7 g of α-thio-β-(2-thienyl)propenoic acid. m.p. 151° C.

C. Preparation of thieno[3,2-b]thien-2-yl carboxylic acid.

The procedures of A and B were repeated to accumulate 393 g (2.1 mole) of α-thio-β-(2-thienyl)-propenoic acid. This acid was dissolved in 8 liters of 1,2-dichloroethane and stirred at 24° C. while a solution of 150 g (2.1 mole) of chlorine in 2400 ml of 1,2-dichloroethane was added dropwise over forty-five minutes. The expected sulfenyl chloride formed immediately as the reaction mixture became deep orange in color. The reaction mixture was stirred at 24° C. for one hour and then was heated at reflux for one hour. Hydrogen chloride was evolved from the reaction mixture during the reflux period. The reaction mixture was cooled to 24° C. and the precipitated solid was collected by filtration, washed with fresh 1,2-dichloroethane and dried to give 289 g of thieno[3,2-b]thien-2-yl carboxylic acid. Melting point after crystallization from ethanol was 220° C.

NMR (CDCl$_3$/DMSOd$_6$) δ7.3 (q, 2H); 8.0 (s, 1H); 9.5 (s, 1H).

D. Preparation of methyl thieno[3,2-b]thien-2-yl formate

Twenty grams of thieno[3,2-b]thien-2-yl carboxylic acid were dissolved in a saturated solution of hydrogen chloride in methanol. The reaction mixture was heated at reflux for sixteen hours and then cooled and concentrated to dryness. The residue was dissolved in dichloromethane, filtered, and the filtrate was concentrated to give 11 g of methyl thieno[3,2-b]thien-2-yl formate. mp 98°–99° C.

NMR (CDCl$_3$) δ3.90 (5, 3H); 7.3 and 7.6 (q, 2H); 8.0 (s, 1H).

Analysis calculated for $C_8H_6O_2S_2$. Theory: C, 48.47; H, 3.05; O, 16.14; S, 32.25. Found: C, 48.29; H, 2.84; O, 16.14; S, 32.34.

E. Preparation of

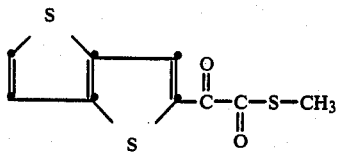

To a cold (5° C.) stirred suspension of 9.0 g of sodium hydride in 100 ml of N,N-dimethylformamide was added dropwise a solution of 19.8 g of methyl thieno[3,2-b]thien-2-yl formate in 100 ml of N,N-dimethylformamide containing 14.5 ml of methyl methylthiomethyl sulfoxide. The reaction mixture was stirred at 5° C. for thirty minutes and for three hours at 25° C. The reaction mixture was again cooled to 5° C. and diluted by addition of 200 ml of methanol. The solvent was removed by evaporation under reduced pressure and the residue was dissolved in ethyl acetate and water. The mixture was made acidic to pH 5.5 with 12N hydrochloric acid. The organic layer was separated and the aqueous acid layer was extracted several times with ethyl acetate. The combined extracts were washed with water, dried and concentrated to dryness to provide 18.0 g of a compound identified as

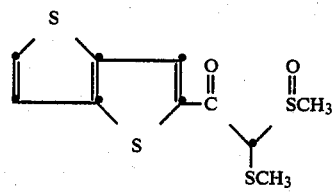

m.p. 144°–145° C.

NMR (DMSOd$_6$) δ2.3 (2s, 3H); 2.8 (2s, 3H); 5.95 (2s, 1H); 8.15 (q, 2H); 8.65 (2s, 1H).

Seventeen grams of the compound thus prepared were added portion-wise to a solution of 59.7 g of acetic anhydride in 271 ml of formic acid. The reaction mixture was heated to 65° C. and stirred for thirty minutes. Two and one-half grams of sodium periodate were added to the reaction mixture and stirring was continued for twenty minutes. The reaction mixture was cooled, concentrated to dryness, and the residue was dissolved in ethyl acetate. The organic solution was washed with 1N sodium hydrosulfite, dried, and the solvent was removed by evaporation to provide 10.0 g of a compound identified as

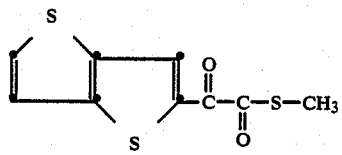

m.p. 94°–96° C.

NMR (CDCl$_3$) δ2.4 (s, 3H); 7.25–7.7 (q, 2H); 8.45 (s, 1H).

F. Preparation of α-methoxyimino-α-thieno-[3,2-b]thien-2-yl acetic acid

A solution of 7.2 g of the thienothiophene from above in 540 ml of methanol containing 30 ml of 1N sodium hydroxide was stirred at 25° C. for thirty minutes. Two and one-half grams of methoxyamine hydrochloride were added in one portion and the solution was stirred at 25° C. for sixteen hours. The reaction mixture was concentrated to dryness and the residue was dissolved in water and acidified to pH 2 with 1N hydrochloric acid. The aqueous acid solution was extracted with ethyl acetate. The extracts were combined, washed with water, dried and the solvent was removed by evaporation under reduced pressure to provide 1.0 g of α-methoxyimino-α-thieno[3,2-b]thien-2-yl acetic acid. m.p. 116°-117° C.

NMR (CDCl₃) δ4.0 (s, 3H); 7.4 (s, 1H); 7.2-7.5 (q, 2H); 12.0 (s, 1H).

PREPARATION 2

α-Methoxyimino-α-(5-chlorothieno[3,2-b]thien-2-yl)acetic acid

The general procedure of Preparation 1 was repeated to prepare methyl thieno[3,2-b]thien-2-yl formate. This compound was reacted with sulfuryl chloride in the presence of p-toluenesulfonic acid in chloroform to produce methyl (5-chlorothieno[3,2-b]thien-2-yl)formate.

NMR (CDCl₃) δ4.0 (s, 3H); 7.1 (s, 1H); 8.0 (s, 1H).

Twenty three and two tenths grams of methyl (5-chlorothieno[3,2-b]thien-2-yl)formate was reacted with methyl methylthiomethyl sulfoxide according to the procedure of Preparation 1E to produce 6.0 grams of a compound identified as a racemic mixture of

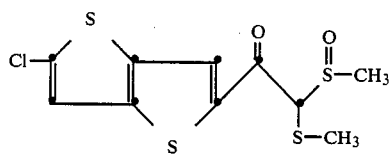

NMR (CDCl₃): δ2.2 (s, 3H); 2.3 (s, 3H); 2.6 (s, 3H); 2.8 (s, 3H); 5.8 (s, 1H); 5.85 (s, 1H); 7.5 (s, 1H); 8.3 (s, 1H); 8.5 (s, 1H).

The above compound was reacted with 0.8 g of sodium periodate in a mixture of 18.8 g of acetic anhydride and 84.6 ml of formic acid to provide 3.5 g of

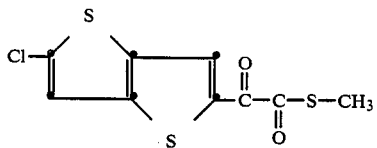

NMR (CDCl₃): δ2.5 (s, 3H); 7.25 (s, 1H); 8.1 (s, 1H).

Three and one-half grams of the above compound were reacted with 1.05 g of methoxyamine hydrochloride in 12.68 ml of 1N sodium hydroxide and 200 ml of methanol to provide α-methoxyimino-α-(5-chlorothieno[3,2-b]thien-2-yl)acetic acid.

NMR (CDCl₃): (DMSOd₆): δ4.0 (s, 3H); 4.2 (s, 3H); 7.2 (s, 2H); 7.25 (s, 1H); 8.1 (s, 1H); 11.3 (s, 1H).

PREPARATION 3

α-Methoxyimino-α-(thieno[2,3-b]thien-2-yl)acetic acid

A. One hundred twelve grams of thiophene-3-carboxaldehyde were combined with 62 g of ethylene glycol in 500 ml of benzene containing 1 g of paratoluenesulfonic acid. The reaction mixture was heated at reflux for sixteen hours and then was washed with water, saturated aqueous sodium bicarbonate and brine. The organic layer was dried and concentrated to provide an oil. The oil was purified by distillation to give 23.4 g of thiophene-3-ethylene acetal of the formula

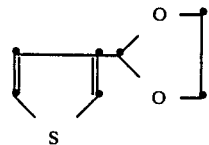

b.p. 55°-60° C. at 0.15 torr.

B. The thiophene-3-ethylene acetal from above was converted to thieno[2,3-b]thien-2-yl carboxylic acid by the method of Gronorvitz and Persson, Acta. Chem. Scand., 1967, 21, 812. mp 230° C.

C. Following the general procedures of Preparation 1, thieno[2,3-b]thien-2-yl carboxylic acid was reacted with methanol and hydrochloric acid to provide methyl thieno[2,3-b]thien-2-yl formate. m.p. 95°-97° C. The ester (7.92 g) was reacted with 6.94 g of methyl methylthiomethyl sulfoxide and 3.6 g of sodium hydride in 80 ml of N,N-dimethylformamide to provide 5.72 of a racemic mixture of

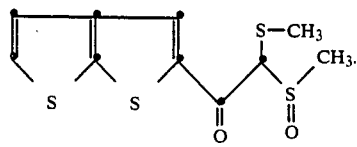

NMR (DMSOd₆): δ2.3 (2s, 3H); 2.8 (2s, 3H); 6.05 (2s, 1H); 7.48 and 7.85 (2q, 2H); 8.5 (2s, 1H). This product was reacted with 0.84 g of sodium periodate in 20 g of acetic anhydride and 90 ml of formic acid to provide 4.0 g of

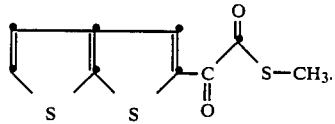

NMR (CDCl₃): δ2.42 (s, 3H); 7.2-7.35 (q, 2H); 8.35 (s, 1H). This product was reacted with sodium hydroxide in methanol and with methoxyamine hydrochloride to afford α-methoxyimino-α-(thieno[2,3-b]thien-2-yl)acetic acid.

NMR (CDCl₃) δ4.01 (s, 3H); 4.3 (s, 3H); 7.0-7.4 (m, 3H); 10.7 (s, 1H).

EXAMPLE 1

7-(Thieno[3,2-b]thien-2-yl)glycylamido-3-methyl-3-cephem-4-carboxylic acid

A solution of 400 mg of α-methoxyimino-α-(thieno[3,2-b]thien-2-yl)acetic acid in 50 ml of acetonitrile containing 15 ml of oxalyl chloride and two drops of N,N-dimethylformamide was stirred at 0° C. for two hours. The reaction mixture was concentrated to dryness by evaporation under reduced pressure to provide α-methoxyimino-α-(thieno[3,2-b]thien-2-yl)acetyl chloride as an oil. The oil was dissolved in 10 ml of fresh acetonitrile and added to a stirred acetonitrile solution of 707 mg of 7-amino-3-methyl-3-cephem-4-carboxylic acid silylated with 2.56 g of bis(trimethylsilyl)trifluoroacetamide (BSTFA). The reaction mixture was stirred at 25° C. for sixteen hours. The reaction mixture was concentrated to dryness to provide an oil which was sonicated for fifteen minutes with 300 ml of saturated aqueous sodium bicarbonate. The mixture was acidified to pH 2.3 by addition of 1N hydrochloric acid. The acid layer was extracted several times with ethyl acetate, and the combined extracts were dried and the solvent was removed by evaporation to provide 970 mg of 7-α-methoxyimino-α-(thieno[3,2-b]thien-2-yl)acetamido-3-methyl-3-cephem-4-carboxylic acid.

The thienothienyl oxime thus prepared (970 mg) was dissolved in 18 ml of methanol to which was added 18 ml of 90% formic acid and 10 ml of water. The reaction mixture was cooled to 0° C. and stirred while 506 mg of zinc dust were added portion-wise over twenty minutes. The reaction mixture was stirred for ninety minutes at 0° C. and filtered. The filtrate was concentrated to dryness and the product was crystallized from ethyl acetate to provide 544 mg of dl-7-(thieno[3,2-b]thien-2-yl)glycylamido-3-methyl-3-cephem-4-carboxylic acid. The product was chromatographed over silica gel eluting with water/acetonitrile/ammonium acetate (89%:10%:1%) to provide:

Example 1A: 7-D-(thieno[3,2-b]thien-2-yl)glycylamido-3-methyl-3-cephem-4-carboxylic acid; and
Example 1B: 7-L-(thieno[3,2-b]thien-2-yl)glycylamido-3-methyl-3-cephem-4-carboxylic acid.

EXAMPLE 2

Following the procedure of Example 1, 827 mg of α-methoxyimino-α-(5-chlorothieno[3,2-b]thien-2-yl)-acetic acid from Preparation 2 was reacted with oxalyl chloride to provide α-methoxyimino-α-(5-chlorothieno[3,2-b]thien-2-yl)acetyl chloride which was reacted with 642 mg of 7-amino-3-methyl-3-cephem-4-carboxylic acid silylated with 2.31 g of BSTFA. The reaction afforded 1.1 g of 7-[α-methoxyimino-α-(5-chlorothieno[3,2-b]thien-2-yl)acetamido]-3-methyl-3-cephem-4-carboxylic acid. The thienothienyl oxime was reacted with 544 mg of zinc dust in formic acid and methanol to provide 1.1 g of 7-(5-chlorothieno[3,2-b]thien-2-yl)glycylamido-3-methyl-3-cephem-4-carboxylic acid. Reverse phase high performance chromatography provided Example 2A: 7-L-(5-chlorothieno[3,2-b]thien-2-yl)glycylamido-3-methyl-3-cephem-4-carboxylic acid; and Example 2B: 7-D-(5-chlorothieno[3,2-b]thien-2-yl)glycylamido-3-methyl-3-cephem-4-carboxylic acid.

EXAMPLE 3

By following the general procedures of Examples 1 and 2, 723 mg of α-methoxyimino-α-(thieno[2,3-b]thien-2-yl)acetic acid from Preparation 3 were converted to the acid chloride which was reacted with silylated 7-amino-3-methyl-3-cephem-4-carboxylic acid. The product, 1.5 g of 7-(α-methoxyimino-α-thieno[2,3-b]thien-2-yl)acetamido-3-methyl-3-cephem-4-carboxylic acid, was reacted with zinc in formic acid and methanol to provide, following high performance liquid chromatography, Example 3A: 7-D-(thieno[2,3-b]thien-2-yl)glycylamido-3-methyl-3-cephem-4-carboxylic acid; and
Example 3B: 7-L-(thieno[2,3-b]thien-2-yl)glycylamido-3-methyl-3-cephem-4-carboxylic acid.

The thienothienylglycyl cephalosporins provided by this invention are valuable antibiotic substances, or intermediates therefor. The compounds are particularly effective against a wide variety of gram-positive bacilli, and are especially useful in the treatment of upper respiratory infections and similar diseases caused by *H. influenza, S. aureus, S. pyogenes*, and the like. The compounds are also effective in the treatment of diseases caused by anaerobic cocci such as *Peptostreptococcus anaerobius,, Peptostrept. intermedius, Peptostrept. productus, Peptococcus osaccharolyticus, P. prevotii, P. avaerobius, Bacteroides fragilis, Propionibacterium acnes, Fusobacterium necrophorum*, and the like.

A typical and preferred compound provided by this invention is 7-(thieno[3,2-b]thien-2-yl)glycylamido-3-methyl-3-cephem-4-carboxylic acid, the compound illustrated in Example 1. The antibacterial activity of this compound and others of the invention has been determined in standard in vitro agar dilution assays against a variety of gram positive microorganisms. The following Tables present typical minimum inhibitory concentrations (MIC's) in µg/ml for several compounds of the invention when evaluated against the indicated microorganisms. MIC's for several known compounds are also presented for comparison.

TABLE 1

| | | Agar Dilution MIC (µg/ml) | | | | | | | |
|---|---|---|---|---|---|---|---|---|---|
| | | Ampi- | Cepha- | Compound of | | | | | |
| Organism | Strain | cillin | lexin | Ex. 1A | Ex. 1B | Ex. 2A | Ex. 2B | Ex. 3A | Ex. 3B |
| Staph. | X1.1 | 0.25 | 4 | .5 | 8 | 1 | .25 | .5 | 1 |
| aureus | V41 | 32 | 128 | 32 | 32 | 64 | 16 | 32 | 64 |
| | X400 | 128 | 128 | 64+ | 64+ | 64+ | 64+ | 64+ | 64+ |
| | S13E | 64 | 128 | 64 | 64 | 32 | 16 | 16 | 64 |
| Staph. epi | EPI1 | 8 | 32 | 16 | 64 | 16 | 4 | 4 | 8 |
| | 222 | 0.25 | 8 | 2 | 16 | 2 | .5 | 1 | 2 |
| Strep. A | C203 | 0.03 | 0.5 | .25 | 16 | 1 | .125 | .25 | 1 |
| Strep. PN | PARK | 0.03 | 2 | 1 | 16 | 2 | .25 | .5 | 2 |
| Strep. D | X66 | 4 | 128 | 64+ | 64+ | 64+ | 64+ | 64+ | 64+ |
| | 2041 | 2 | 128 | 64+ | 64+ | 64+ | 64 | 64+ | 64+ |
| H. influ. | C.L. | 0.5 | 8 | 64 | 64 | 64 | 32 | 8 | 16 |
| | 76 | 16 | 8 | 2 | 8 | 2 | 2 | 2 | 1 |
| E. coli | N10 | 8 | 8 | 64+ | 64+ | 64+ | 64+ | 64+ | 64+ |
| | EC14 | 4 | 4 | 64+ | 64+ | 64+ | 64+ | 64 | 64+ |
| | TEM | 128 | 8 | 64+ | 64+ | 64+ | 64+ | 64+ | 64+ |
| Klebsiella | X26 | 16 | 4 | 8 | 64+ | 64 | 16 | 8 | 16 |
| | KAE | 128 | 128 | 64+ | 64+ | 64+ | 64+ | 64+ | 64+ |
| | X68 | 16 | 8 | 64+ | 64+ | 64+ | 64+ | 64+ | 64+ |

The data in the above Tables clearly demonstrate the potent antibacterial activity possessed by the compounds of this invention.

In addition to possessing potent antibacterial activity against a wide variety of microorganisms, particularly gram positive organisms and anaerobes, the compounds of this invention also have very favorable pharmacokinetics in animals.

The favorable pharmacokinetics of the compounds provided by this invention, coupled with their excellent antibacterial activity and oral absorption, make them particularly attractive agents for the treatment of a number of diseases of bacterial origin. The compounds are especially well suited for the treatment of outpatients, and especially for subjects suffering from mild upper respiratory infections caused by gram positive microorganisms.

The treatment of animals suffering from bacterial diseases, or suspected of developing a bacterial infection, is thus another embodiment of this invention. The antibacterial method of treatment provided by this invention will be practiced by administering an antibacterially effective amount of a thienothienylglycyl cephalosporin antibiotic as defined herein to an animal in need of treatment. The method can be practiced therapeutically or prophylactically. The amount of active antibiotic to be administered according to the method will vary depending upon the particular compound selected for use, the severity of the disease being treated or guarded against, the individual undergoing treatment, and related factors commonly encountered with such treatments. Normally, however, the compounds will be administered at a dose of about 0.5 to about 50 mg/kg of animal body weight, and more preferably at a rate of about 1 to about 10 mg/kg. Such amounts will be administered once each day, or more often as needed to treat the particular disease or subject undergoing treatment according to the present method. A typical daily dose for an average adult human will be about 200 to about 500 mg per day.

The antibiotic compounds provided by this invention are active by both the oral and parenteral routes of administration, and accordingly can be formulated for any such desired route of administration. Such formulations constitute yet another embodiment of this invention. The formulations of this invention will comprise from about 0.1 to about 95 percent by weight of an active thienothienylglycyl cephalosporin antibiotic of the invention, admixed with a pharmaceutically acceptable carrier, diluent or excipient therefor. Typical formulations will contain from about 10 to about 60 percent by weight of active ingredient, and more preferably about 20 to about 50 percent.

For convenient oral administration, the compounds can be admixed with any of a number of diluents, excipients and carriers commonly employed in oral formulations, and molded into tablets, pills, troches, or encapsulated into gelatin capsules. Typical carriers, diluents and excipients commonly employed include potato starch, corn starch, sucrose, dextrose, microcrystalline cellulose, dicalcium phosphate, alginic acid, acacia; lubricants such as magnesium stearate; binders such as gum tragacanth or gelatin; and flavoring agents such as peppermint oil, cherry or strawberry flavoring, oil of wintergreen, and the like. The compounds can also be formulated as syrups or elixirs employing common diluents such as a fatty oil, methyl or propyl parabens, suitable dyes and flavoring agents. The compounds can also be formulated in the form of a buccal seal, lozenge or other suitable device for sustained controlled delivery of the active ingredient over a prolonged period.

The antibiotics of the invention can also be formulated for parenteral administration, for example via the intravenous, intramuscular or subcutaneous routes, as well as the transdermal route. Such compositions normally will contain from about 0.1 to about 20.0 percent by weight of active ingredient. Typical excipients, diluents and carriers for parenteral formulations include isotonic saline, dilute aqueous dextrose, the polyhydric aliphatic alcohols or mixtures thereof, for instance glycerin, propylene glycol, polyethylene glycol, and the like. Parenteral solutions may also contain preservatives such as phenethylalcohol, methyl and propyl parabens, thimerosal and the like. If needed, about 0.05 to about 0.20 percent by weight of an antioxidant such as sodium metabisulfite or sodium bisulfite can also be employed. For intravenous use, preferred formulations will employ an initial concentration down to about 0.05 to about 0.25 mg/ml of active ingredient, and for intramuscular injection, a preferred concentration of active ingredient is about 0.25 to about 0.50 mg/ml.

Examples of typical pharmaceutical formulations contemplated by this invention include the following.

EXAMPLE 4

Formulation of Oral Suspension

| Ingredient | Amount |
|---|---|
| Sodium D-7-(thieno[3,2-b]thien-2-yl-glycylamido)-3-chloro-3-cephem-4-carboxylate | 500 mg |
| Sorbitol solution (70% N.F.) | 40 ml |
| Sodium benzoate | 150 mg |
| Saccharin | 10 mg |
| Cherry flavor | 50 mg |
| Distilled water q s ad | 100 ml |

The sorbitol solution is added to 40 ml of distilled water and the thienothienylglycyl cephalosporin is suspended thereon. The saccharin, sodium benzoate, and flavoring are added and dissolved. The volume is adjusted to 100 ml with distilled water. Each ml of syrup contains 5 mg of the thienothienylglycyl cephalosporin antibiotic. This oral formulation is ideally suited for pediatric use.

EXAMPLE 5

Preparation of 250 mg capsule

| Ingredient | Amount |
|---|---|
| 7-(5-Chlorothieno[3,2-b]thien-2-yl-glycylamido)-3-methyl-3-cephem-4-carboxylic acid | 250 mg |
| Lactose | 150 mg |
| Corn starch | 100 mg |
| | 500 mg |

The ingredients are blended to uniformity and encapsulated into gelatin capsules. Such capsules are orally administered at the rate of about one each day for the treatment of upper respiratory bacterial infections, including pharyngitis and tonsillitis.

EXAMPLE 6

Preparation of Parenteral Solution

In a solution of 700 ml of propylene glycol and 200 ml of distilled water for injection is dissolved 20.0 grams of D-7-(thieno[2,3-b]thien-2-ylglycylamido)-3-methoxymethyl-3-cephem-4-carboxylic acid, hydrochloride. The pH of the solution is adjusted to 5.5 with hydrochloric acid, and the volume is made up to 1000 ml with distilled water. The formulation is sterilized, filled into 5.0 ml ampoules each containing 2.0 ml (representing 40 mg of active ingredient) and sealed under nitrogen.

We claim:

1. A compound of the formula

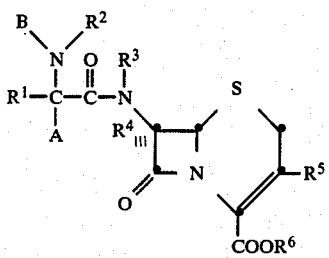

wherein:

$R^1$ is

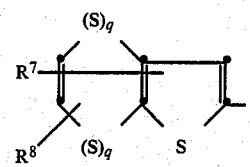

in which $R^7$ and $R^8$ independently are hydrogen, halo, hydroxy, $C_1$-$C_4$ alkyl, $C_1$-$C_4$ alkoxy, nitro, amino, $C_1$-$C_4$ alkanoylamino, $C_1$-$C_4$ alkylsulfonylamino, and when $R^7$ and $R^8$ are on adjacent carbon atoms, they can be taken together to form methylenedioxy;

p and q independently are 0 or 1, provided p plus q equal 1;

A and B both are hydrogen, or taken together complete a double bond;

$R^2$ is hydrogen, an amino protecting group, hydroxy, or methoxy, and $R^3$ is hydrogen, or $R^2$ and $R^3$ taken together are

where M and N independently are $C_1$-$C_4$ alkyl;

$R^4$ is hydrogen, methoxy or methylthio;

$R^5$ is hydrogen, methoxy, methyl, halo, methoxymethyl, or vinyl;

$R^6$ is hydrogen, a salt forming cation group, or a carboxy protecting group;

and the pharmaceutically acceptable acid addition salts thereof; with the proviso that $R^2$ is hydroxy or methoxy only when A and B complete a double bond, and that A and B both are hydrogen when $R^3$ is other than hydrogen.

2. The compound of claim 1 wherein $R^2$ and $R^3$ are taken together to form

3. The compound of claim 1 wherein A and B are taken together to complete a double bond.

4. The compound of claim 3 wherein $R^2$ is methoxy.

5. The compound of claim 4 wherein $R^5$ is methyl or chloro.

6. The compound of claim 1 wherein A and B both are hydrogen.

7. The compound of claim 6 wherein $R^1$ is

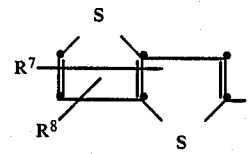

8. The compound of claim 7 wherein $R^7$ is hydrogen or halo.

9. The compond of claim 8 wherein $R^7$ is hydrogen.

10. The compound of claim 9 wherein $R^4$ is hydrogen.

11. The compound of claim 10 wherein $R^5$ is methyl or chloro.

12. The compound of claim 11 wherein $R^6$ is hydrogen or a salt forming cation.

13. The compound of claim 12, said compound being D-7-(thieno[3,2-b]thien-2-yl)glycylamido-3-methyl-3-cephem-4-carboxylic acid.

14. The compound of claim 12 wherein $R^8$ is halo.

15. The compound of claim 14 wherein $R^8$ is chloro.

16. The compound of claim 14 wherein $R^8$ is fluoro.

17. The compound of claim 12 wherein $R^8$ is hydroxy.

18. The compound of claim 12 wherein $R^8$ is $C_1$-$C_4$ alkoxy.

19. The compound of claim 12 wherein $R^8$ is amino.

20. The compound of claim 10 wherein $R^5$ is hydrogen.

21. The compound of claim 10 wherein $R^5$ is methoxymethyl.

22. The compound of claim 10 wherein $R^5$ is vinyl.

23. The compound of claim 6 wherein $R^1$ is

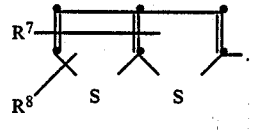

24. The compound of claim 23 wherein $R^7$ is hydrogen.

25. The compound of claim 24 wherein $R^4$ is hydrogen.

26. The compound of claim 25 wherein $R^5$ is methyl or chloro.

27. The compound of claim 26 wherein $R^6$ is hydrogen or a salt forming cation.

28. A method of treating bacterial infections in animals comprising administering an effective amount of an antibacterial compound of claim 1.

29. The method of claim 28 employing a compound wherein A, B, $R^2$, $R^3$ and $R^4$ all are hydrogen.

30. The method of claim 29 employing a compound wherein $R^6$ is hydrogen or a salt forming cation.

31. The method of claim 30 employing a compound wherein $R^5$ is methyl or chloro.

32. The method of claim 31 employing a compound wherein $R^1$ is

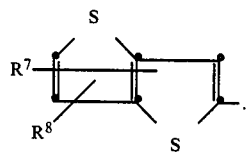

33. The method of claim 32 employing a compound wherein $R^7$ is hydrogen.

34. The method of claim 33 employing D-7-(thieno[3,2-b]thien-2-yl)glycylamido-3-methyl-3-cephem-4-carboxylic acid.

35. The method of claim 33 employing a compound wherein $R^8$ is fluoro.

36. The method of claim 33 employing a compound wherein $R^8$ is chloro.

37. An antibacterial pharmaceutical formulation comprising a compound of claim 1 admixed with a pharmaceutical carrier, diluent or excipient.

38. The formulation of claim 37 employing a compound wherein A, B, $R^2$, $R^3$ and $R^4$ all are hydrogen.

39. The formulation of claim 38 employing a compound wherein $R^6$ is hydrogen or a salt forming cation.

40. The formulation of claim 39 employing a compound wherein $R^5$ is methyl or chloro.

41. The formulation of claim 40 employing a compound wherein $R^1$ is

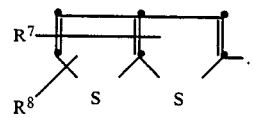

42. The formulation of claim 41 employing a compound wherein $R^7$ is hydrogen.

43. The formulation of claim 42 employing a compound wherein $R^8$ is hydrogen.

44. The formulation of claim 42 employing a compound wherein $R^8$ is halo.

* * * * *